(12) United States Patent
Li et al.

(10) Patent No.: US 9,150,866 B2
(45) Date of Patent: Oct. 6, 2015

(54) APPARATUS AND METHOD FOR SINGLE-CYCLE SELECTION OF APTAMERS

(71) Applicant: The Governors of the University of Alberta, Edmonton (CA)

(72) Inventors: Xing-Fang Li, Edmonton (CA); X. Chris Le, Edmonton (CA); Yanming Liu, Edmonton (CA)

(73) Assignee: The Governors of the University of Alberta, Edmonton, AB (CA)

( * ) Notice: Subject to any disclaimer, the term of this patent is extended or adjusted under 35 U.S.C. 154(b) by 0 days.

(21) Appl. No.: 14/012,816

(22) Filed: Aug. 28, 2013

(65) Prior Publication Data

US 2014/0148356 A1    May 29, 2014

Related U.S. Application Data

(60) Provisional application No. 61/693,878, filed on Aug. 28, 2012.

(51) Int. Cl.
*C12N 15/115*    (2010.01)

(52) U.S. Cl.
CPC .......... *C12N 15/115* (2013.01); *C12N 2310/16* (2013.01); *C12N 2330/30* (2013.01)

(58) Field of Classification Search
None
See application file for complete search history.

(56) References Cited

U.S. PATENT DOCUMENTS 8,507,203 B2 *   8/2013   Le et al. .................. 435/6.1

FOREIGN PATENT DOCUMENTS

WO    WO2011060557    *  5/2011

* cited by examiner

*Primary Examiner* — Juliet Switzer
*Assistant Examiner* — Sahana Kaup
(74) *Attorney, Agent, or Firm* — Marsh Fischmann & Breyfogle LLP; Jonathon A. Szumny (57) ABSTRACT

A method for single-cycle selection of aptamers is provided. More specifically, a method comprising single-cycle selection of aptamers for proteins blotted on a membrane is provided. In some embodiments, the present methods can comprise a deoxyribonuclease I (DNase I) mediated aptamers selection strategy that may be capable of isolating strong binding aptamers for target proteins from a crude protein extract. Aptamers selected using the present method are further provided. More specifically, the presently selected aptamers may be thermally stable, modifiable and easily produced through single-cycle synthesis process. The present aptamers may provide unique affinity reagents for use in diagnosing and detecting infectious disease (for example Hepatitis B), for research and biochemical studies (e.g. into molecular mechanisms). Further, the present aptamers may be utilized to develop unique assays or kits for clinical application, such as monitoring disease treatment and outcome.

4 Claims, 12 Drawing Sheets

Sequence A-18
Tm=54.5 °C
ΔG=-8.9 kal/mol

Figure 7B

Sequence A-38
Tm=46.8 °C
ΔG=-10.7 kal/mol

Figure 8A

Sequence A-19
Tm=56.5 °C
ΔG=-10.2 kal/mol

Figure 8B

Sequence A-23
Tm=46.2 °C
ΔG=-9.2 kal/mol

Figure 8C

Sequence A-9
Tm=67.1 °C
ΔG=-12.8 kal/mol

Figure 9

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
agcagcacag aggtcagatg                                                 20

<210> SEQ ID NO 2
<211> LENGTH: 20
<212> TYPE: DNA
<213> ORGANISM: Artificial Sequence
<220> FEATURE:
<223> OTHER INFORMATION: PCR primer

<400> SEQUENCE: 2
ttcacggtag cacgcatagg                                                 20

<210> SEQ ID NO 3
<211> LENGTH: 80
<212> TYPE: DNA
<213> ORGANISM: Artificial Sequence
<220> FEATURE:
<223> OTHER INFORMATION: randomized region flanked on both sides by PCR
      primers

<400> SEQUENCE: 3
agcagcacag aggtcagatg aggcctggtg atcgtgccca ggccatatga gcaaggaacc     60
cctatgcgtg ctaccgtgaa                                                 80

<210> SEQ ID NO 4
<211> LENGTH: 80
<212> TYPE: DNA
<213> ORGANISM: Artificial Sequence
<220> FEATURE:
<223> OTHER INFORMATION: randomized region flanked on both sides by PCR
      primers

<400> SEQUENCE: 4
agcagcacag aggtcagatg tttccgaggg agtggaatta gcaaggtgga agtgtttcta     60
cctatgcgtg ctaccgtgaa                                                 80

<210> SEQ ID NO 5
<211> LENGTH: 80
```

```
<212> TYPE: DNA
<213> ORGANISM: Artificial Sequence
<220> FEATURE:
<223> OTHER INFORMATION: randomized region flanked on both sides by PCR
      primers

<400> SEQUENCE: 5
agcagcacag aggtcagatg acatctagaa ccaacggttc tgtttgatga gaattcggcc     60
cctatgcgtg ctaccgtgaa                                                 80

<210> SEQ ID NO 6
<211> LENGTH: 80
<212> TYPE: DNA
<213> ORGANISM: Artificial Sequence
<220> FEATURE:
<223> OTHER INFORMATION: randomized region flanked on both sides by PCR
      primers

<400> SEQUENCE: 6
agcagcacag aggtcagatg ttgcatacgc caaacaagca ttgacaaggt aaccctgggc     60
cctatgcgtg ctaccgtgaa                                                 80

<210> SEQ ID NO 7
<211> LENGTH: 80
<212> TYPE: DNA
<213> ORGANISM: Artificial Sequence
<220> FEATURE:
<223> OTHER INFORMATION: randomized region flanked on both sides by PCR
      primers

<400> SEQUENCE: 7
agcagcacag aggtcagatg gttacatgcg cagtagccga cgtactctgg taaaaggtag     60
cctatgcgtg ctaccgtgaa                                                 80
```

APPARATUS AND METHOD FOR SINGLE-CYCLE SELECTION OF APTAMERS

CROSS-REFERENCE TO RELATED PATENT APPLICATIONS

This patent application claims the benefit of U.S. Provisional Patent Application No. 61/693,878, filed on Aug. 28, 2012, the entire teachings and disclosure of which are incorporated by reference herein.

TECHNICAL FIELD

An apparatus and method for single-cycle selection of aptamers is provided. More specifically, an apparatus and method comprising single-cycle selection of aptamers for proteins blotted on a membrane is provided. Aptamers selected using the present apparatus and method are further provided.

BACKGROUND

Nucleic acid aptamers are single-stranded DNA or RNA molecules capable of binding to small molecules, proteins, and whole cells with high affinity and selectivity. Aptamers have been widely applied both as therapeutic reagents and as promising tools for molecular diagnostics and basic research, and are commonly selected in vitro from large libraries of DNA or RNA sequences using Systematic Evolution of Ligands by Exponential Enrichment (SELEX).

It is known that the selection of aptamers having high affinities and specificities for specific proteins can be done from a large library by incorporating modified dUTP in the SELEX process. The process, however, typically requires multiple cycles (8-20 rounds) of partitioning, separation, and PCR amplification steps. As such, several attempts have been made to improve the time and resources required for the SELEX process, including attempts to achieve the selection of aptamers using a single cycle.

One such attempt, known as the capillary electrophoresis SELEX (CE-SELEX), may be used to select an aptamer for h-Ras protein in a single cycle by repeated, highly efficient separation of the protein-bound sequences from the unbound sequences. However, due to the limited injection volume of the CE-SELEX system, over 97% of the DNA sequence diversity was lost, although initial DNA library contained $2 \times 10^{12}$ ssDNA sequences.

Another such attempt, which involves a magnetic microfluidic chip (M-SELEX) can, in principle, be applied to any protein target. The M-SELEX strategy may achieve extremely high selection stringency by exposing a very small quantity of target proteins to a DNA library during the partitioning step. This method is limited, however, to microscale sample volumes and may be subject to the risk of compromising sequence diversity. This method also requires immobilization of the target molecules onto micromagnetic beads prior to aptamer selection.

There is a need to develop a consistent and reliable single-cycle aptamer selection strategy that takes full advantage of the large DNA library diversity and this is amenable to common laboratory practice. Such a system may be capable of directly selecting aptamers for proteins on a membrane, and may not be limited by sample volumes. Such a system may further be capable of being integrated into common protein separation techniques used in biochemistry laboratories such as, gel electrophoresis and membrane blotting. Both of Musheev, M.: Krylov, S. N. Analytica Chim. Acta 2005, 564, 91-96 and Oh, S. S.; Plakos, K.: Lou, X.; Xiao, Y.; Soh, H. T. 2010, Proc. Natl. Acad. Sci. U.S.A. 107 (32) 14053-14058 are incorporated by reference herein in their entirety.

SUMMARY

An apparatus and method for single-cycle selection of aptamers is provided. More specifically, an apparatus and method comprising single-cycle selection of aptamers for proteins blotted on a membrane is provided. In one embodiment, the present apparatus and method comprise a deoxyribonuclease I (DNase I) mediated aptamers selection strategy that may be capable of isolating strong binding aptamers for target proteins from a crude protein extract.

Aptamers selected using the present apparatus and method are further provided. More specifically, the present selected aptamers may be thermally stable, modifiable and easily produced. The present aptamers may provide unique affinity reagents for use in diagnosing and detecting infectious disease, for research and biochemical studies (e.g. into molecular mechanisms). Further, the present aptamers may be utilized to develop unique assays or kits for clinical application, such as monitoring disease treatment and outcome.

In one embodiment, a DNase I assisted membrane partitioning method for rapid selection of aptamers against HBV core protein in one cycle is provided. The present apparatus and method may comprise the use of DNase I to increase stringency and selectivity, and the use of western-blotted protein on membranes to allow for the use of a small amount of target protein for washing and elution, thereby potentially eliminating the need for multiple rounds of selection. Using gel electrophoresis separation and western blot to prepare the target protein from the extracts for selection makes this approach potentially useful for selecting aptamers against multiple proteins in cell lysate or other mixtures.

Broadly stated, in some embodiments, an aptamer capable of binding specifically to a Hepatitis B virus biomarker is provided.

In some embodiments, the aptamer can comprise a nucleic acid, such as DNA or ssDNA. In some embodiments, the Hepatitis B virus biomarker can comprise a HBV protein, such as a HBV nucleocapsid protein, a HBV core protein, as an example, HBcAg. In some embodiments, the aptamer can be selected from a library using a single-cycle selection method.

Broadly stated, in some embodiments, a method for detecting a Hepatitis B virus biomarker using an aptamer is provided.

Broadly stated, in some embodiments, a composition for detecting a Hepatitis B virus biomarker, comprising an aptamer according is provided.

Broadly stated, in some embodiments, a kit for detecting a Hepatitis B virus biomarker, comprising an aptamer is provided.

Broadly stated, in some embodiments, a method is provided for single-cycle selection of aptamers, comprising: incubating an isolated protein with a nucleic acid library to allow nucleic acids to bind to the protein to form a nucleic acid-protein complex; washing away unbound nucleic acids; digesting the unbound and weakly bound nucleic acids with a nuclease; and washing away further unbound nucleic acids to select a nucleic acid aptamer remaining bound to the protein.

In some embodiments, the nucleic acid aptamer comprises a sequence selected from the group consisting of SEQ ID NO:3, SEQ ID NO:4, SEQ ID NO:5, SEQ ID NO:6, and SEQ ID NO:7.

DESCRIPTION OF THE EMBODIMENTS

It is known that deoxyribonucleic acid (DNA) can be protected from the cleavage by DNase I when the DNA is tightly bound to proteins. As such, DNase I may be utilized to digest and deplete unbound and weakly bound ssDNA sequences from a given selection pool, resulting in the identification of strong binding aptamers in a single cycle. An apparatus and method for one-cycle DNase I assisted membrane partitioning of high affinity, highly selective aptamers for a target protein (e.g. HBV core protein) is provided. Further, sub-nM level aptamers with consensus sequences obtained using this method are provided.

The present apparatus, method and aptamers are further exemplified by way of the following Example 1, including Supporting Information, Appendix 1 and Appendix 2.

Example 1

Figure 1A:
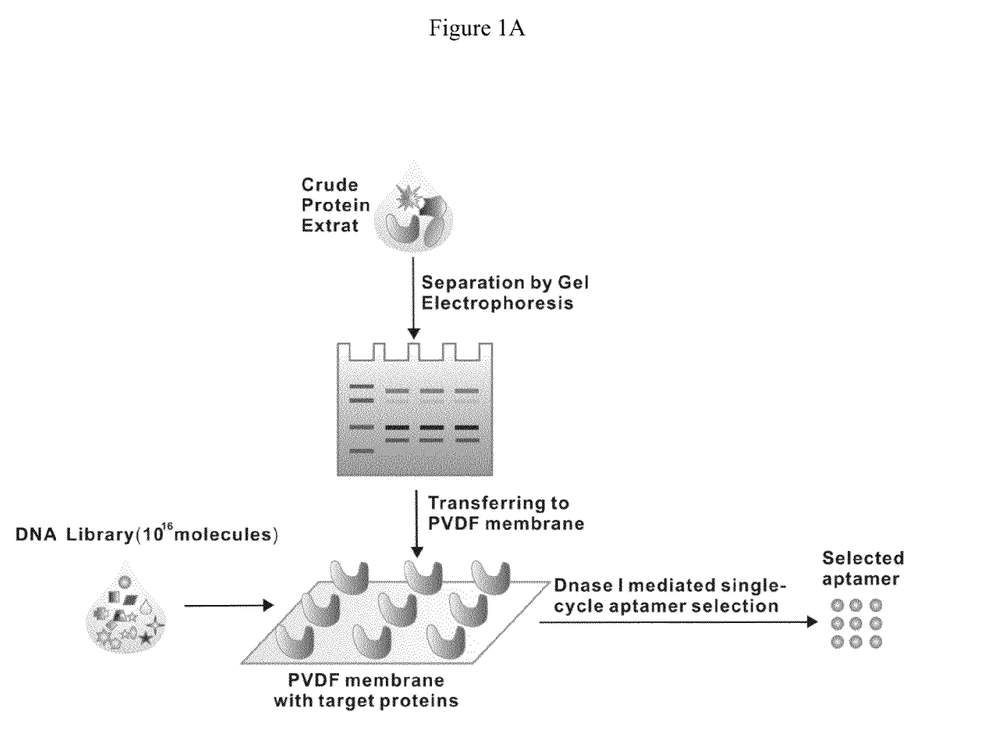
FIG. 1A provides a schematic of the present apparatus and method.
Figure 1B:
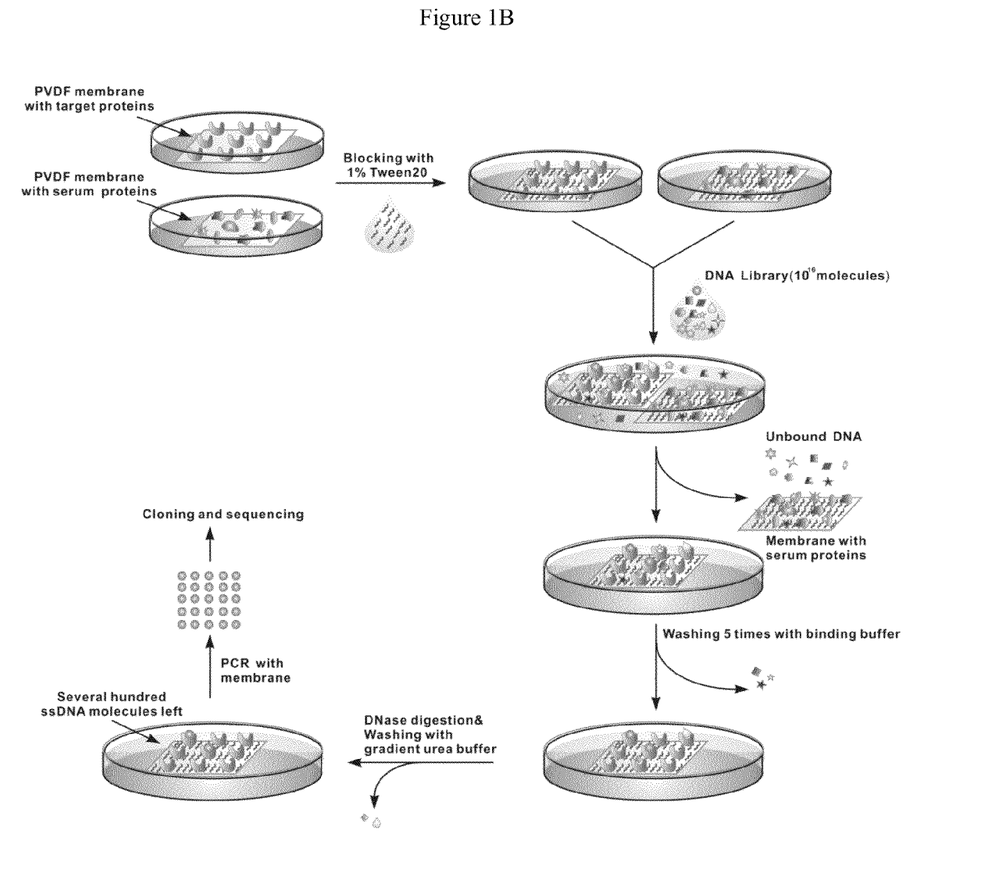
FIG. 1B depicts the present single-cycle aptamer selection strategy as mediated by DNase I.

An apparatus and method for single-cycle selection of aptamers for proteins blotted on a membrane is provided. For example, FIG. 1 provides a schematic of the present single-cycle aptamer selection strategy for a target protein from a crude extract protein. By way of explanation, target proteins may be electrophoretically separated from a crude protein extract and blotted onto a PVDF membrane. A strip of the membrane containing the blotted protein (target-protein) and a second strip of the membrane blotted with serum proteins (matrix-membrane) may be blocked with 1% Tween 20. Both membrane strips are then co-incubated in a well with a ssDNA library containing 10 copies each of $10^{15}$ individual, random DNA sequences (this may be done for 2 hours at room temperature). The inclusion of serum proteins may serve as the "counter selection" strategy to remove sequences that bind to the matrix.

The target membrane is then removed from the unbound ssDNA and the matrix membrane, and transferred to a second well where it may be washed (e.g. approximately 5 times) with the binding buffer. Subsequently, this membrane may be treated with DNase I, followed by urea buffer wash (7, 8, and 9M) to remove unbound and weakly bound ssDNA. As a result, the unbound and weakly bound sequences are removed while the strongly bound DNA sequences remain on the membrane. This may result because washing with increasing concentrations of urea enables efficient removal of weakly bound sequences, retaining only the strongly bound DNA aptamers. Selected aptamers may then be identified by PCR amplifying, cloning and sequencing the remaining sequences bound to the target.

In other words, the present apparatus and method attempt to isolate the strongest binding aptamer against a target protein in a biological mixture using a single-cycle approach. The present apparatus and method comprise firstly obtaining the protein from the biological mixture, which involves the use of a native polyacrylamide gel electrophoresis to separate the protein from the mixture, and then to immobilize the protein onto a polyvinylidene fluoride (PVDF) membrane through electro-blotting. Given that the protein-bound DNA can be protected from DNase digestion, DNase I digestion and gradient washing with urea buffer can be used to remove the unwanted weak or unbound ssDNA from the membrane, thereby isolating the strongest binding aptamer.

By way of further example, aptamers against Hepatitis B virus (HBV) core protein (HBcAg, 21 KD, theoretical pI 9.93), a unit of the nucleocapsid of HBV, were obtained. The HBcAg target protein was selected herein because it is known to be essential for the replication of HBV and serves as a good biomarker for active Hepatitis B. Although the HBcAg protein is tested and discussed herein, it is understood that any target proteins, particularly those serving as biomarkers of known diseases, may be selected.

In some embodiments, the aptamers may be part of a kit which includes all necessary aptamers and reagents for testing a biological sample. In some embodiments, the kit for detecting the presence of a Hepatitis B virus biomarker can comprise an aptamer or a panel of aptamers, reagents for detecting the binding of the aptamer or panel of aptamers to a Hepatitis B virus biomarker, and one or more supports. In some embodiments, selected aptamers can be incorporated into rapid antigen detection tests.

In order to select the aptamers against HBcAg, the target protein in a crude sample was separated using a native polyacrylamide gel electrophoresis (PAGE) and then blotted on a PVDF membrane. A strip of the membrane containing HBcAg was cut off and used in the process of aptamer selection. Further information may be found in the "Supporting Information" provided below.

Figure 2:
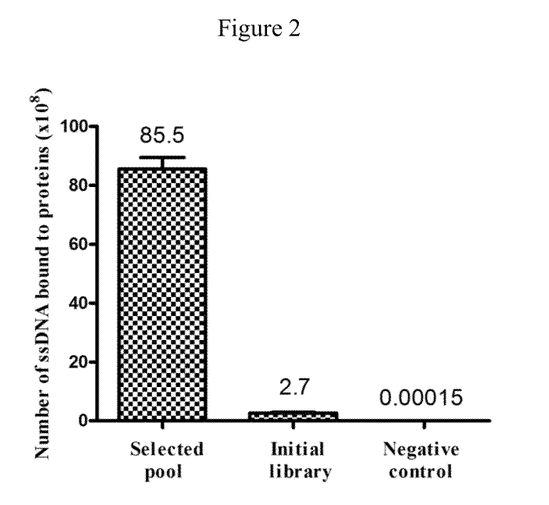
FIG. 2 provides the affinity of the ssDNA pool for HBcAg before (initial library) and after (selected library) the present apparatus and method. Error bars represent one standard deviation from duplicate analyses.

Following the DNase I digestion step, it was noted that the number of DNA molecules remaining on the membrane was reduced from $10^{16}$ to $10^4$. By comparison, washing the membrane with 3.5M urea buffer for 30 minutes, instead of DNase I digestion, could only reduce DNA molecules on the membrane to $10^7$, thereby suggesting that DNase I digestion is highly efficient in removing unbound and weakly bound DNA sequences from the membrane. Indeed, having regard to FIG. 2, the amount of protein-bound DNA molecules were over 30-fold higher when the selected pool was used than when the initial library was used. HBcAg (5 nM) was incubated with equal molar concentrations of either the initial DNA library or the aptamer pool from the single-cycle selection process. The number of ssDNA molecules bound to the HBcAg protein was determined using the affinity real-time PCR assay. Negative controls did not contain HBcAg but other conditions were kept the same as for the selected pool or initial library.

Aptamers having the highest binding affinities were selected by washing the target membrane with increasing concentrations of urea buffer (7-9M). After washing the membrane with 9M urea, it was noted that approximately a few hundred (~500) DNA molecules remained on the membrane (see Supporting Information). These sequences represent a pool of aptamers that bind strongly to the target protein on the membrane.

Figure 3:
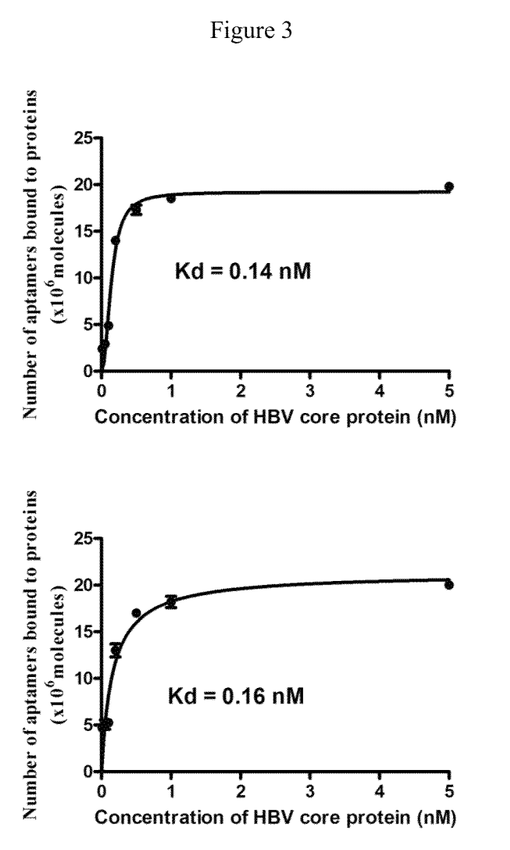
FIG. 3 shows two examples of one exemplary target protein (e.g. HBcAg) binding to two aptamers (A-18, top; and A-38, bottom). The dissociation constant (Kd) values were estimated to be 0.14 nM for aptamer A-18 and 0.16 nM for aptamer A-38. Error bars represent one standard deviation from duplicate analyses.

The present system and method may further be utilized to analyze and determine secondary structures of the selected aptamers, thereby providing information relating to the molecular structure necessary to bind target proteins. For example, from the selected aptamer pool, approximately 60 sequences were found containing the 80-nt insert after PCR amplification, cloning and sequencing. Analyses of these sequences showed that most of them (43/60) could form stable secondary structures with predicted free energies of formation below-6.9 KJ and Tm above 45° C. To identify the sequences having strong affinity to HBcAg, binding affinity of the 43 sequences using the affinity qPCR binding assay was measured. Five aptamers were found to have strong binding to HBcAg (see Supporting Information herein). FIG. 3 depicts two examples of HBcAg binding to two aptamers.

The present apparatus and method aim to provide an efficient and practical single-cycle aptamer selection strategy that takes advantages of large sequence diversity and high selection stringency. Using this strategy, aptamers for HBcAg were selected with high binding affinity (Kd at the sub-nM levels). It should be noted that the present apparatus and method are not limited to selecting aptamers for a single protein, and may be combined with established separation techniques, e.g. two-dimensional electrophoresis. To achieve the high selection stringency, other DNA nucleases may also be used, alone or in combination with DNase I, to digest the ssDNA sequences that are not protected by strong binding to the target of interest.

Supporting Information

The foregoing Example is further supported by the following details and information:

Initial ssDNA Library

An 80-nt single-stranded DNA library consisting of a 40-nt randomized region flanked on both sides by forward primer Pf (5'-AGCAGCACAGAGGTCAGATG-3') (SEQ ID NO:1) and reverse primer Pr (5'-TTCACGGTAGCACGCATAGG-3') (SEQ ID NO:2) was used. A Pr primer modified with a phosphate group at the 5' end (Prph) was prepared. The initial ssDNA pool and the primers used in this study were obtained from Integrated DNA Technologies™ (Coralville, Iowa).

Aptamer Selection Procedures

One strip of membrane blotted with HBcAg (target-membrane) and one strip of membrane spotted with human serum proteins (matrix-membrane) were blocked with 1% Tween 20 that was diluted in a binding buffer. The binding buffer contained 20 mM Tris-HCl (pH 7.6), 5 mM KCl, 100 mM NaCl, 5 mM $MgCl_2$, 1 mM $CaCl_2$ and 0.02% Tween 20. This blotting step was carried out at room temperature (RT) for 1 h, followed by three times washing with the binding buffer. The ssDNA library (approximately 10 copies each of $10^{15}$ individual sequences) in 1 mL binding buffer was rendered single-stranded before use via heating at 90° C. for 10 min, cooling at 0° C. for 10 min, and incubating at RT for 8 min. The ssDNA library was used to incubate with one target-membrane strip and one matrix-membrane strip. After incubation at RT for 2 h with mild (50 rpm) shaking, the target-membrane was transferred into a second well and washed five times with 1 mL binding buffer to remove unbound DNA sequences. The target-membrane was then treated with 50 μL of a solution of DNase I (Invitrogen) consisting of 1×DNase I reaction buffer and 5 U DNase I. The DNase I digestion was conducted at RT for 1 hr and then stopped by adding 5 μL 25 mM EDTA. After digestion, to further remove weakly bound DNA sequences, the target membrane was further washed with urea buffers (pH 8.0), containing 40 mM Tris-HCl, 10 mM EDTA, 0.02% Tween 20 with each of the 7M, 8M or 9M urea. Specifically, the target-membrane was sequentially washed with each of the 7 M, 8 M, and 9 M urea buffer for three times. Finally the target-membrane was washed once again with distilled deionized water prior to the sequence amplification step.

PCR Amplification and Purification

The selected ssDNA pool on the membrane was directly PCR amplified. A total volume of a 50-μL PCR reaction included 1×PCR reaction buffer, 2.8 mM $MgCl_2$, 1 μM of each primer, 0.2 mM dNTPs, 5% DMSO, 1.25 U of platinum Taq DNA polymerase, 32.45 μL deionized water, and a fraction (1/10) of the target-membrane after all washing steps. Thermocycling (MJ Mini Gradient Thermocycler, Bio-Rad Laboratories™, Hercules, Calif.) parameters were 94° C. for 5-min denaturation, followed by 31 cycles of denaturation at 94° C. for 30 s, annealing at 56° C. for 30 s, and extension at 72° C. for 30 s. After the last cycle of PCR, a final extension step was at 72° C. for 10 min.

The PCR products (10 μL) were separated using gel electrophoresis on a 12% native polyacrylamide gel and 1×TBE buffer (Bio-Rad Protean III) at 60-120 V. The gels were stained with ethidium bromide and photographed under UV light. All PCR products were purified using Qiagen MinElute PCR Purification Kit™ (Qiagen Inc., Valencia, Calif.) according to the recommended procedures. Estimation of the amount of DNA remaining on the membrane after different treatments was performed using PCR-PAGE method.

In the present study, PCR conditions were optimized to eliminate both shorter and longer PCR byproducts. 5%

DMSO in PCR mixture was used to eliminate shorter PCR byproducts. To eliminate longer PCR byproducts, PCR conditions were optimized using a simple approach as previously reported. It has been demonstrated that longer PCR byproducts start to accumulate when dsDNA products reaching $10^{11}$-$10^{12}$ molecules when a 80-nucleotide long DNA library is amplified. PCR byproducts are not detectable on the gel when $X_n$ is equal to $10^{11}$ molecules. Therefore, the n can be pre-calculated to avoid generation of longer byproducts.

Figure 4:
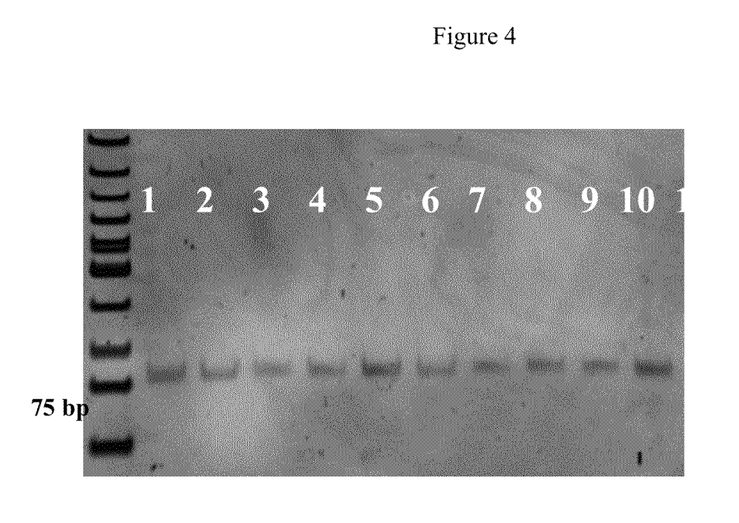
FIG. 4 is a gel image showing PCR product amplified from ssDNA library containing different numbers of random sequences. Lanes: 1, Low molecular weight DNA ladder; 2, $2.2 \times 10^{10}$ molecules (4 cycles); 3, $2.2 \times 10^9$ molecules (7 cycles); 4, $2.2 \times 10^8$ molecules (10 cycles); 5, $2.2 \times 10^7$ molecules (13 cycles); 6, $2.2 \times 10^6$ molecules (17 cycles); 7, $2.2 \times 10^5$ molecules (20 cycles); 8, $2.2 \times 10^4$ molecules (23 cycles); 9, $2.2 \times 10^3$ molecules (26 cycles); 10, 220 molecules (28 cycles); 11, 22 molecules (30 cycles)
Figure 5:
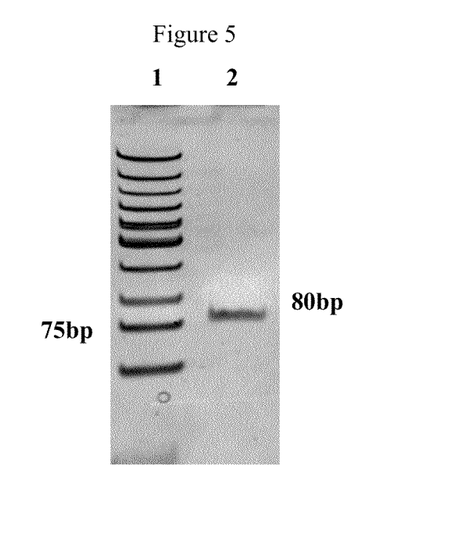
FIG. 5 is a gel image of PCR products amplified from ssDNA molecules retained on the target membrane, after DNase I treatment and gradient urea buffer (7-9 M) washings. Lane-1 is low molecular weight DNA ladder, and Lane-2 is the PCR product from a 1/10 piece of the treated target membrane after amplification (31 cycles). The abundance of remaining ssDNA on membrane is estimated to be ~500 DNA molecules according to the equation: $X_0 = 10^{11}/2^n$.

According to PCR amplification formula: $X_n = X_0 \times 2^n$ where $X_n$ is PCR product after n cycles, $X_0$ is the initial copies of DNA molecules, and n is the PCR cycle number. When $X_0$ is $10^{19}$, $10^9$, $10^8$, $10^7$, $10^6$, $10^5$, $10^4$, and $10^3$, n should be 4, 7, 10, 13, 17, 20, 23 and 26, respectively. To confirm this, a set of DNA samples was prepared by 10× serial dilution of the ssDNA library. PCR cycles were then set with pre-calculated n for the corresponding template concentrations. All PCR products of the set of DNA samples showed only one band on the gel (FIG. 4). Because of elimination of byproducts, the equation ($X_0 = 10^{11}/2^n$) can be used to estimate the amount of template by PCR. This method was used to estimate the DNA retained on the target membrane. FIG. 5 shows an example of the PCR products (80-nt) amplified from the DNA molecules retained on the target membrane after one cycle selection.

Cloning, Sequencing, and Secondary Structural Analysis of Aptamers

After amplification and purification of the selected aptamer pool, *E. coli* DH5α-T1$^R$ cells using TOPO TA cloning kit (Invitrogen™) was used to clone these sequences. Eighty colonies were randomly picked up for sequencing analysis (Molecular Biology Services Unit, Department of Biological Sciences at the University of Alberta). Among these colonies, sequencing results confirmed that 60 colonies contained the 80-nt insert. The secondary structures of these 60 sequences were analyzed using Oligoanalyzer 3.0 (IDT), with input conditions of room temperature (25° C.), 100 mM NaCl and 5 mM MgCl$_2$. Secondary structure analysis showed that 43 sequences can form stable secondary structures with the formation free energy ΔG below −6.9 KJ and Tm above 45° C.

Generation of ssDNA for Affinity Tests

To determine binding affinity, PCR was first used to amplify the selected aptamer pool with the forward primer and the reverse primer described above. The reverse primer was modified with a phosphate group at the 5' end to enable a following digestion of the reverse-strand of PCR product (dsDNA) with lambda exonuclease enzyme. For this cleavage reaction, every 1 μg of dsDNA was treated with 25 units of lambda exonuclease in 1× lambda exonuclease reaction buffer at 37° C. for 4 h. The digestion was then stopped by raising the temperature to 75° C. for additional 10 min. Subsequently, the ssDNA was then purified with the QIAEXII system (Qiagen)™ and quantified using UV-visible measurement at 260 nm.

Determination of Binding Affinities of the Selected ssDNA Pool and Individual Selected Sequences to HBcAg Using Affinity Real-Time PCR Assay The binding affinities of the selected aptamer pool and the individual aptamers were measured using a known real-time qPCR affinity assay. Briefly, the selected aptamer pool, individual aptamer, and the initial library were heat denatured prior to the incubation with HBcAg. An amount of 5 nM of ssDNA (selected sequence pool or the initial ssDNA library) was incubated with 5 nM of HBV core protein for 1 h at RT. In parallel, negative controls consisting of the initial library without HBcAg were included. Then the protein was coupled on the Ni-NTA plate (Thermo scientific nunc), followed by one wash step with the binding buffer. The bound ssDNA were eluted by binding buffer containing 300 mM imidazole (elution buffer), followed by 10 times dilution with 10 mM Tris-HCl buffer at pH 8.5. The number of ssDNA in the eluent was quantified by the real-time qPCR.

Figure 6:
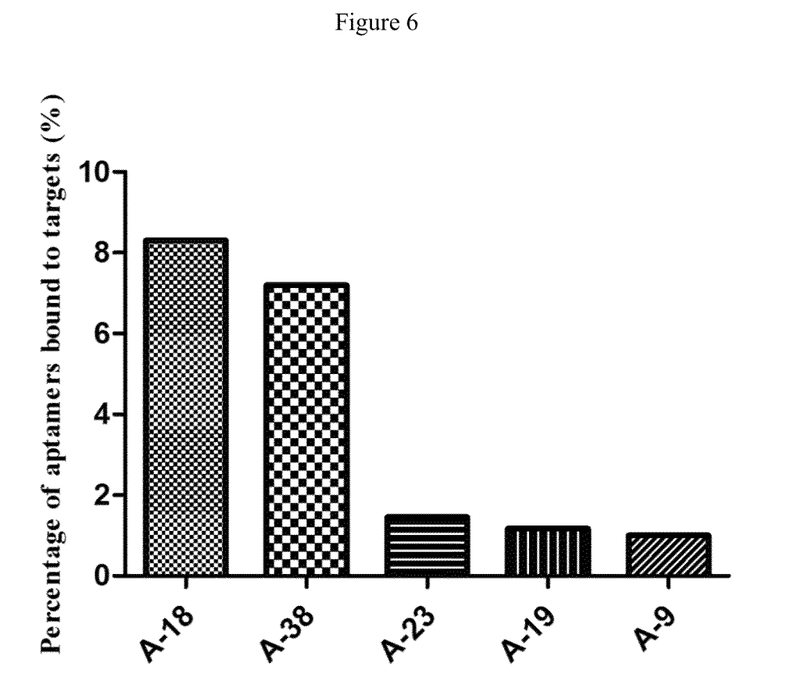
FIG. 6 shows the percentages of the five selected aptamers binding to the target protein HBcAg, demonstrating that A-18 and A-38 have the strongest binding affinity.
Figure 7A:
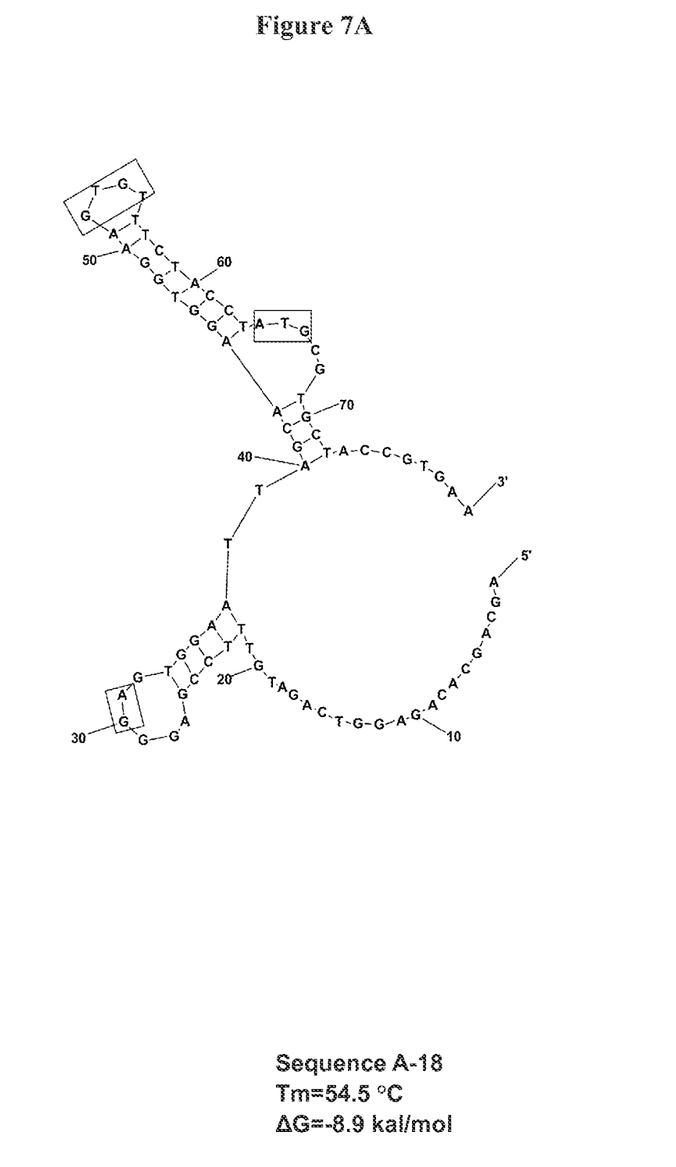
FIG. 7A shows the predicted secondary structure of sequence A-18 with ΔG and Tm.
Figure 7B:
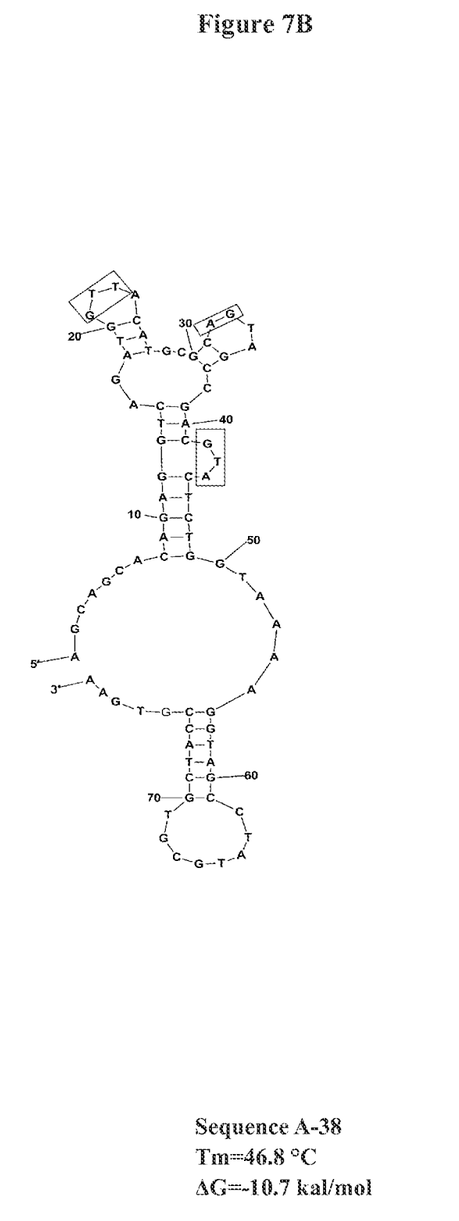
FIG. 7B shows the predicted secondary structure of sequence A-38 with ΔG and Tm.
Figure 8A:
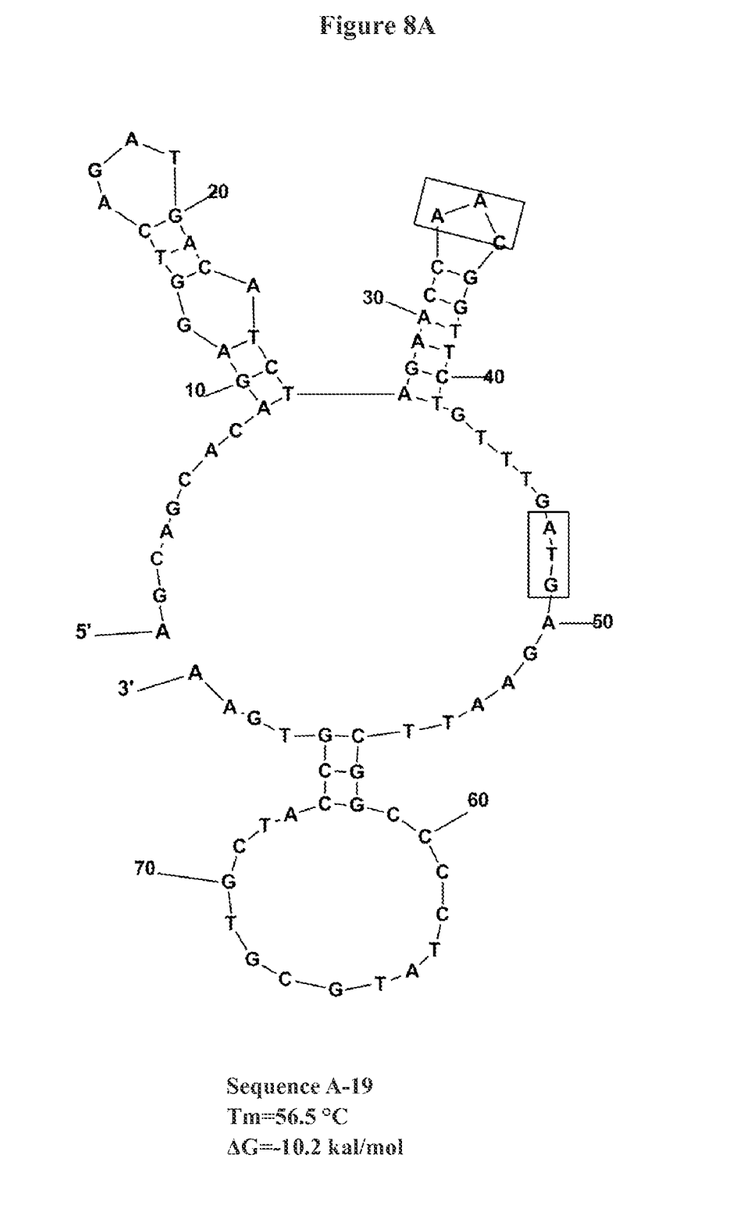
FIG. 8A shows the predicted secondary structure of the aptamer A-19 with ΔG and Tm.
Figure 8B:
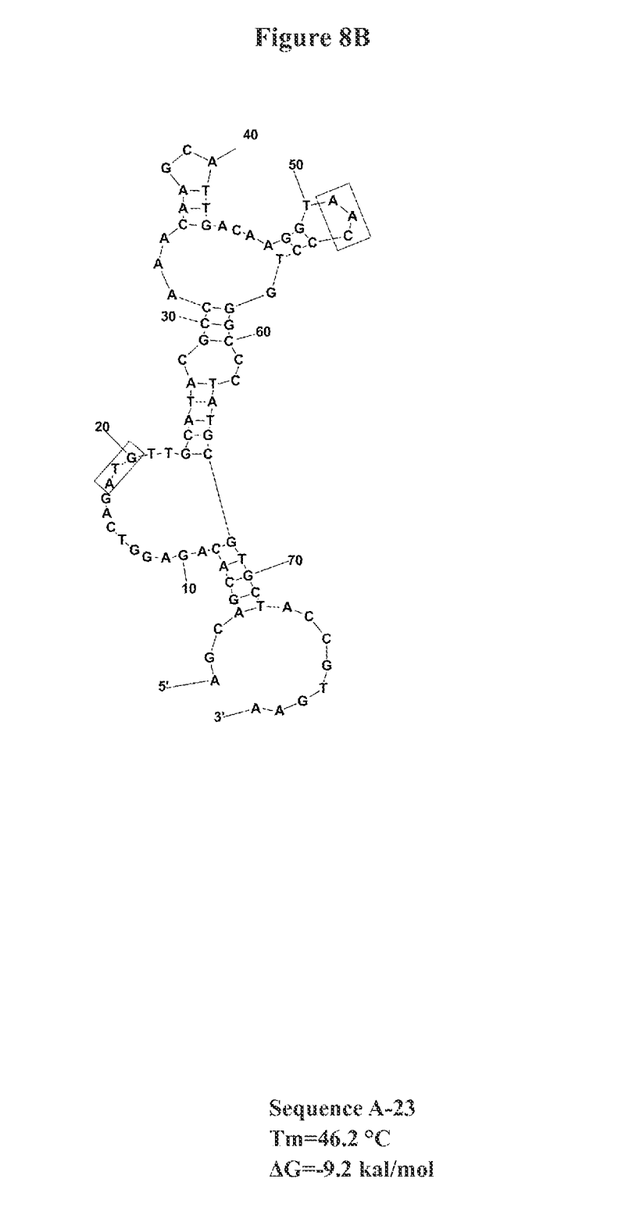
FIG. 8B shows the predicted secondary structure of the aptamer A-23 with ΔG and Tm.
Figure 8C:
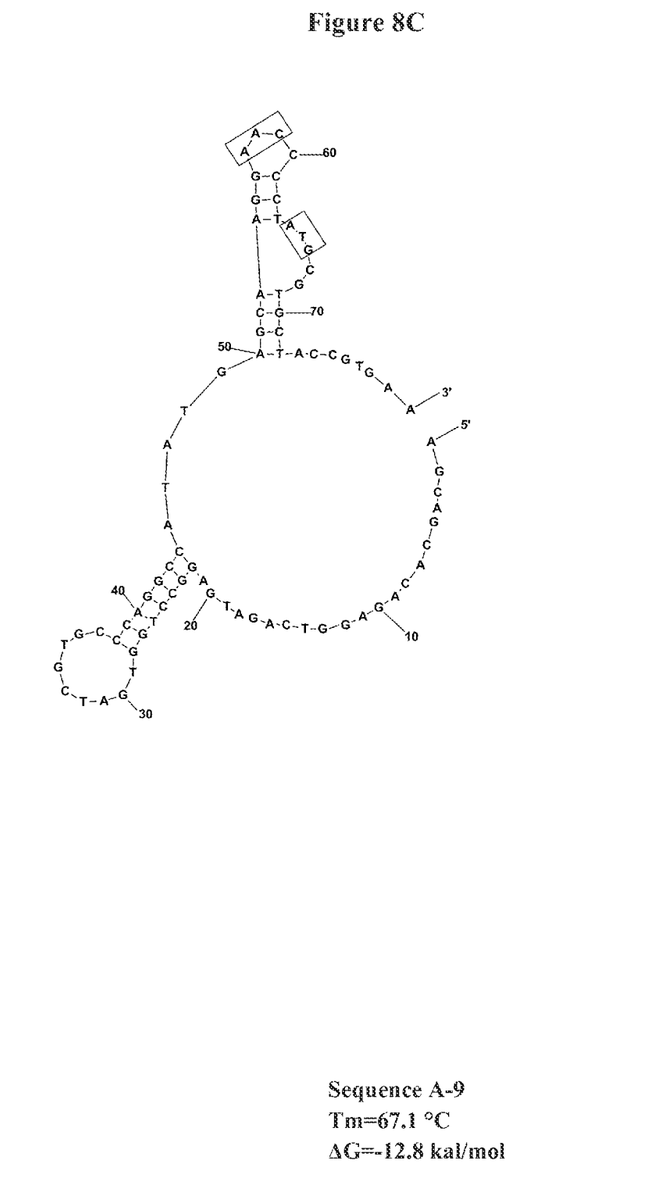
FIG. 8C shows the predicted secondary structure of the aptamer A-9 with ΔG and Tm.

Affinities of the selected individual sequences were also evaluated using this method. Affinities of the selected sequences were compared by the percentage of bound DNA for each sequence after incubation of 7.6 nM HBcAg with 1 nM of the individual selected sequences. The percentage was calculated by $X_{sample}/X_{total} = 2^{Ct(total)-Ct(sample)}$ which was inferred according to real-time PCR formula: $X_n = X_0(1+E)^n$ ($X_n$=PCR product after cycle n, $X_0$=initial copy number, E=amplification efficiency, n=cycle number), assuming E=1, Xn=threshold, the equation is simplified to: $X_0$=threshold/$2^{Ct}$, so $X_{sample}/X_{total} = 2^{Ct(total)-Ct(sample)}$. Five aptamers had were found to have strong binding to HBcAg (Table 1, FIG. 6), and sequences A-18 and A-38 have the strongest binding to HBcAg (Table 2 and FIGS. 7, 8), as much as 8.3% and 7.2% of the DNA bound to the target, respectively, while other three sequences can also bind to the target.

Table 2 shows.

TABLE 1

The affinities of the five selected aptamers to HBcAg

| Sequence number | Background (Negative control, (Ct) | Aptamer bound to targets (Ct) | Total aptamer (Ct) | $Ct_{Background} - Ct_{aptamer\ bound}$ | Percentage of aptamer bound to targets (Xsample/ Xtotal)$^a$ |
|---|---|---|---|---|---|
| A-18 | 15 | 12.10 | 8.41 | 2.90 | 8.3% |
| A-38 | 14.44 | 11.61 | 7.81 | 2.83 | 7.2% |
| A-23 | 17.32 | 14.90 | 8.80 | 2.42 | 1.45% |
| A-19 | 17.82 | 14.94 | 8.52 | 2.88 | 1.17% |
| A-9 | 21.75 | 19.42 | 12.78 | 2.33 | 1% |

$^a$Xsample/Xtotal = $2^{Ct\text{-}total - Ct\ aptamer\ bound}$

TABLE 2

The sequences of five selected HBcA2 aptamers

| Name | Sequence$^a$ |
|---|---|
| A-9 (SEQ ID NO: 3) | 5'AGCAGCACAGAGGTCAGATGAGGCCTGGTGATCGTGCC CAGGCCATATGAGCAAGGAAC<u>CCTATGCGTGCTACCGTG AA</u>-3' |
| A-18 (SEQ ID NO: 4) | 5'AGCAGCACAGAGGTCAGATGTTTCCGAGGGAGTGGAAT TAGCAAGGTGGAAGTGTTTCTA<u>CCTATGCGTGCTACCGTG AA</u>-3' |
| A-19 (SEQ ID NO:5) | 5'AGCAGCACAGAGGTCAGATGACATCTAGAACCAACGGT TCTGTTTGATGAGAATTCGGCC<u>CCTATGCGTGCTACCGTG AA</u>-3' |
| A-23 (SEQ ID NO:6) | 5'AGCAGCACAGAGGTCAGATGTTGCATACGCCAAACAAG CATTGACAAGGTAACCCTGGGC<u>CCTATGCGTGCTACCGTG AA</u>-3' |
| A-38 (SEQ ID NO: 7) | 5'AGCAGCACAGAGGTCAGATGGTTACATGCGCAGTAGCC GACGTACTCTGGTAAAAGGTAG<u>CCTATGCGTGCTACCGTG AA</u>-3' |

$^a$Primer regions are underlined.

Figure 9:
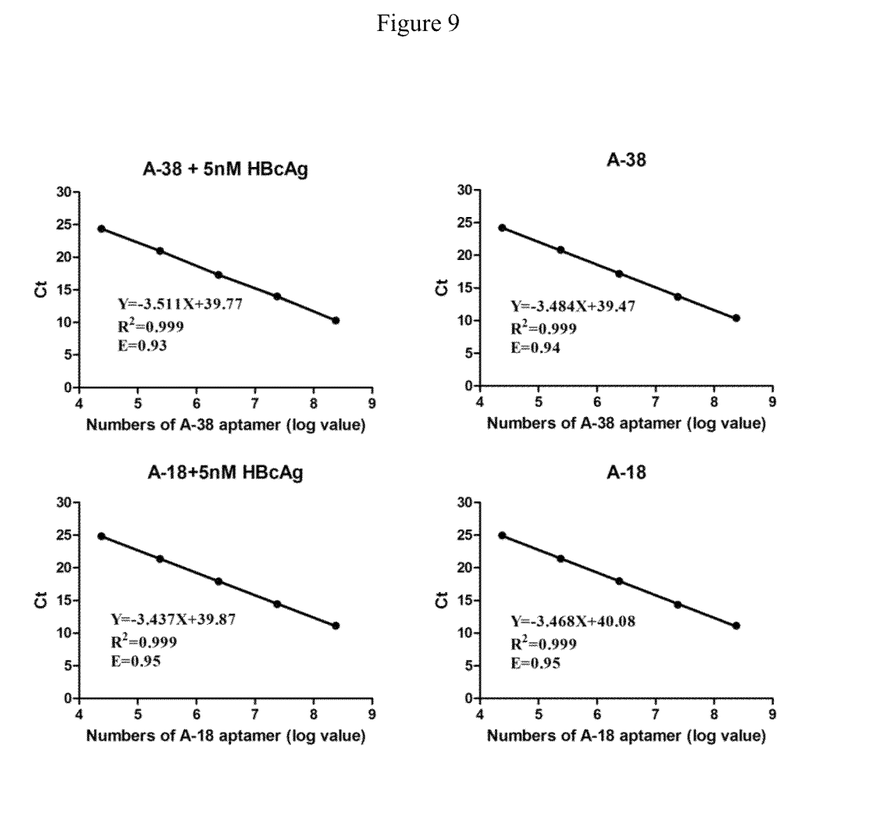
FIG. 9 shows standard curves from the quantitative PCR analyses of aptamers A-18 and A-38 in the presence (Left) or absence (Right) of 5 nM of HBcAg. The log values of the numbers of aptamer molecules are plotted against the corresponding Ct values. E: amplification efficiency; $E = 10^{-1/slope} - 1$. The PCR efficiencies from these standard curves showed that PCR amplification remains constant 93-95% with or without the presence of the target molecules.

The evaluation of $K_d$ values of the two sequences having the highest binding affinity was then performed in the following manner. Each aptamer at 0.1 nM was incubated with the target protein in a range of concentrations (0.1 nM to 5 nM) in binding buffer. After incubation at RT for 1 h, the amount of the aptamer bound to the target was determined using the real time qPCR method. A real-time qPCR standard curve was obtained (FIG. 9) for each sequence to quantify the amount of bound ssDNA. A negative control was used to subtract background measurements. Finally a non-linear curve-fitting algorithm was used to determine the IQ (FIG. 9).

All real-time qPCR experiments were performed using the SYBR Green ER qPCR supermix-UDG kit (Invitrogen™). Each PCR reaction mixture includes 10 μL of the SYBR Green ER qPCR supermix universal, 0.3 μL of each of the forward and the reverse primers (20 μM), 1 μL of DMSO, 0.04 μL of ROX reference dye, 4 μL of template, and 4.36 μL of sterile distilled water. PCR negative controls consisting of all the PCR reagents without template were included in each set of experiment. The real-time qPCR protocol consisted of an initial denaturation temperature at 95° C. for 10 min, followed by 40 cycles of denaturing at 95° C. for 15 s and annealing at 56° C. for 1 min. Each sample was run in duplicate wells, and $C_t$ values were averaged from the two reactions.

Although a few embodiments have been shown and described, it will be appreciated by those skilled in the art that various changes and modifications might be made without departing from the scope of the invention. The terms and expressions used in the preceding specification have been used herein as terms of description and not of limitation, and there is no intention in the use of such terms and expressions of excluding equivalents of the features shown and described or portions thereof, it being recognized that the invention is defined and limited only by the claims that follow.

We claim:

1. A single stranded DNA aptamer comprising a secondary structure, wherein the secondary structure is capable of binding specifically to Hepatitis B virus protein, HBcAg, wherein the single-stranded DNA comprises a sequence selected from the group consisting of SEQ. ID. NO: 3; SEQ. ID. NO: 4; SEQ. ID. NO: 5; SEQ. ID. NO: 6; and SEQ. ID. NO: 7.

2. A method for detecting Hepatitis B virus protein HBcAg comprising: contacting a sample with a single stranded DNA aptamer according to claim 1 and detecting binding of the aptamer to the target.

3. A composition for detecting a Hepatitis B virus biomarker, comprising the aptamer according to claim 1.

4. A kit for detecting a Hepatitis B virus biomarker, comprising the aptamer according to claim 1.

* * * * *